United States Patent [19]  
Endo

[11] 4,436,725  
[45] Mar. 13, 1984

[54] PHYSIOLOGICALLY ACTIVE NOVEL SUBSTANCE MUTASTEIN AND PROCESS FOR ITS PRODUCTION

[75] Inventor: Akira Endo, Tokyo, Japan

[73] Assignee: Godo Shusei Co., Ltd., Tokyo, Japan

[21] Appl. No.: 352,069

[22] Filed: Feb. 24, 1982

[30] Foreign Application Priority Data

Mar. 6, 1981 [JP] Japan ............................... 56-31985

[51] Int. Cl.$^3$ ...................... A61K 35/00; A61K 7/16; C12D 1/02
[52] U.S. Cl. ..................................... 424/116; 424/49; 435/171
[58] Field of Search ................... 424/116, 49; 435/171

[56] References Cited

FOREIGN PATENT DOCUMENTS 82101569 of 0000 European Pat. Off. ............ 424/116  
568386 9/1975 Switzerland ........................ 424/119

OTHER PUBLICATIONS

Article: "ANTIBIOTICS, Origin, Nature and Properties", by T. Korzybski et al., Pergamon Press, vol. II, pp. 1230–1235.

Primary Examiner—Jerome D. Goldberg  
Attorney, Agent, or Firm—Oblon, Fisher, Spivak, McClelland & Maier

[57] ABSTRACT

A physiologically active novel substance designated as Mutastein is disclosed, which has the following specific physiological properties:

(1) it has a molecular weight of at least 200,000, and when subjected to gel-filtration with Sephadex G-100 and Sephallose 6B, it will be eluted in the void volume;

(2) its ultraviolet spectrum: FIG. 1;

(3) its infrared spectrum: FIG. 2;

(4) it has a proteinous nature and contains about 10% of saccharide;

(5) it is soluble in water and a saline solution, but it will be salted out from a saturated solution containing about 30% of ammonium salfate; and it is insoluble in acetone, ethanol, ethylacetate and benzene, (6) it dissolves in a buffer solution having a pH 7 or over, but it precipitates at a pH of from 3 to 3.5, (7) it is stable when heat-treated at pH 9, at 100° C. for 10 minutes, (8) its elementary analysis: C: about 44%, H: about 7%, and N: about 12%, (9) its color reactions: Phenol-surfuric acid color reaction (orange), and Folin's color reaction (blue). This substance can be prepared by culturing the Mutastein-producing strain belonging to the genus Aspergillus, and isolating the Mutastein from the culture medium.

8 Claims, 2 Drawing Figures

PHYSIOLOGICALLY ACTIVE NOVEL SUBSTANCE MUTASTEIN AND PROCESS FOR ITS PRODUCTION

BACKGROUND OF THE INVENTION

This invention relates to a physiologically active novel substance having activities to inhibit dextran synthesis and to prevent teeth from decaying, and also to a process for its production.

It is known that insoluble dextran is synthesized from sucrose by oral bacteria and it deposits together with the bacteria themselves to form tartar or dirt on the teeth, which is one of the causes for tooth decay. It has been considered possible to prevent the tooth decay by inhibiting the bacterial dextran synthesis which will cause tooth decay.

SUMMARY OF THE INVENTION

It is accordingly an object of the present invention to provide a physiologically active novel substance which can inhibit the bacterial dextran synthesis.

It is another object of the invention to provide a process for producing the substance of the just-mentioned type.

The present inventor has conducted the extensive searches for substances which inhibit the dextran synthesis in culture media for microorganisms, and has discovered a physiologically active substance in a culture medium of the genus Aspergillus. Thus, the present invention provides the substance which is produced by a microorganism and which is useful as a tooth decay preventive.

It has been found that this substance inhibits a plaque formation by Streptococcus mutans which is a representative cariogenic bacterium. This substance will hereinafter be referred to as "Mutastein".

The present invention relates further to a process for culturing a fungus and collecting Mutastein from the cultured medium, and particularly to a process for culturing a strain of the genus Aspergillus and collecting Mutastein from the culture.

DETAILED DESCRIPTION OF THE INVENTION

Figure 1:
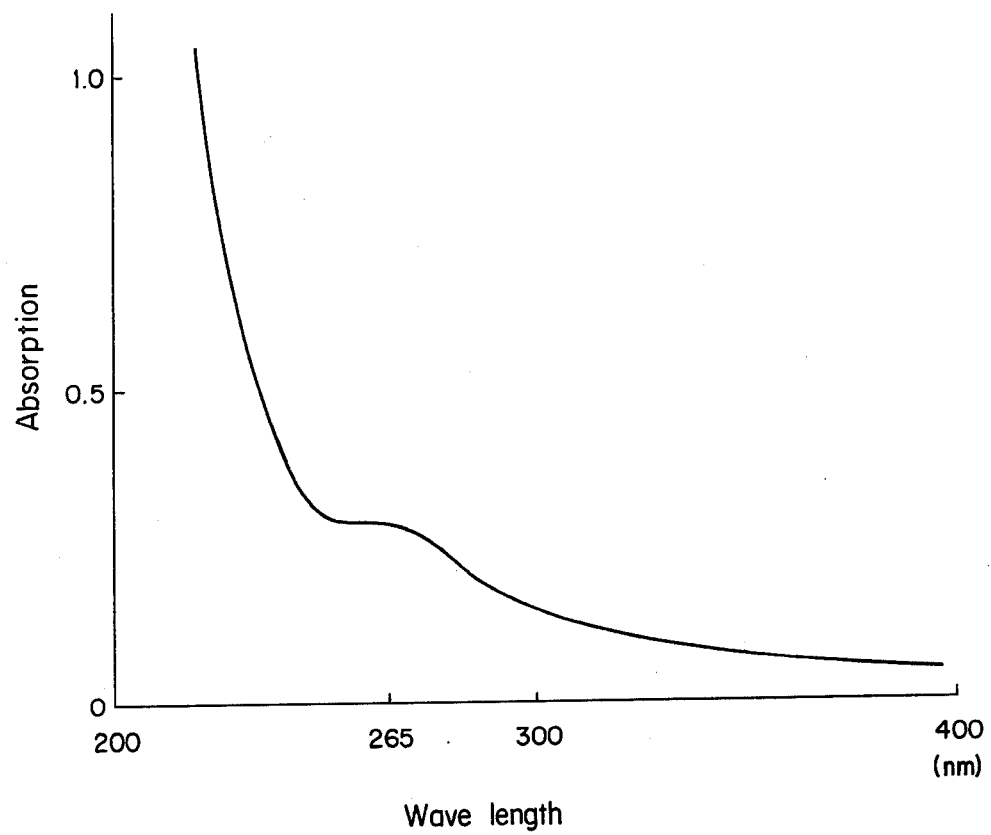
FIG. 1 shows the ultraviolet absorption spectrum of Mutastein.

The microorganisms which may be used in the present invention, are Mutastein-producing strains belonging to the genus Aspergillus. The present inventor has found that particularly useful as such a strain is, for instance, Aspergillus terreus M 3328. This strain was deposited at Fermentation Research Institute Agency of Industrial Science and Technology Ministry of International Trade and Industries Yatabe-Machi, Ibaraki, Japan 305, under Deposit No. 5891 (FERM-P No. 5891). FERM BP-101 is accession number given by the International Depository Authority.

This strain was isolated from a soil of Musashino city, Tokyo, by the preent inventor, and its mycological characteristics are as follows:

Characteristics of the colonies

Growth rate:

It grows fairly fast at 25° C. on a potato dextrose agar medium, a Czapek—Dox ager medium and a corn meal agar medium to form colonies having diameters of 2.8, 3.5 and 4.3 cm, respectively. At 37° C., the growth is inhibitive or extremely inhibitive on each one of these three media. The optimal growth temperature is from 24° to 28° C. The growth is observed in the above media at pH 2 to 8. However, the preferred pH range for the growth is from pH 3 to pH 7.

Growth pattern:

(1) On a potato dextrose agar medium: At 25° C., the basal mycelial layer is more or less thin and has shallow radial grooves. Light brown to dark brown, velvet-like, a number of conidial head formations; the secretory fluid having a light amber colour; and the back side of the colonies being dark yellow to brown. At 37° C., the basal mycelial layer is swollen in a mountain-like shape and has radial grooves, being light brown, velvet-like, floccose at the center; the conidial head formations being small in number; the secretory fluid being dark amber; and the back side of the colonies being dark reddish brown.

(2) On Czapek—Dox agar medium: At 25° C., the basal mycelial layer is flat, light brown to brown, velvet-like, the center portion being felt-like or floccose, the conidial head formation being slightly poor, the secretory fluid being amber, and the back side of the colonies being dark reddish brown. At 37° C., the growth pattern is similar to that on the potato dextrose medium at 37° C.

(3) In a corn meal agar medium: At 25° C., the basal mycelial layer is extremely thin and flat, almost colourless, brown conidial heads lying sporadically, and the back side of the colonies being also colourless.

Microscopic characteristics

Conidial generation:

Conidial heads: An elongated cylindrical shape, red brown, 80 to 150×30 to 50$\mu$ when cultured on a slide, and 400 to 500×50$\mu$ on the colonies as observed by a stereoscopic microscope.

Conidiophores: 50 to 180×4.0 to 5.4$\mu$, most of them being more or less bent, smooth surface, colourless, the front tip being swelled to form a terminal cyst.

Terminal cysts: A hemispherical shape having a diameter of 8 to 9.5$\mu$, Metulae being formed on the upper half portion; during the growing stage those having a few metulae and not yet matured into a hemispherical shape.

Metulae: About 4×2$\mu$, colourless.

Phialides: About 5.5×2$\mu$, colourless.

Conidia: Phialide type conidia, long and chained, the diameter being 1.9 to 2.4$\mu$, spherical, smooth surface.

On the basis of the above colonial and microscopic characteristics, this strain was identified as Aspergillus terreus.

Mycological characteristics of Aspergillus terreus are described in the following literatures: Bacteria Picture Book, Last Volume, edited by Shun-ichi Utagawa, Keisuke Tsubaki, et al, pages 1039 to 1040, 1978 (Kodansha, Scientific) and C. Thom, M. B, Church: American Journal of Botany, Vol. 5, page 85, 1918.

It is obvious that any other strain of Aspergillus is available in this invention so long as it has Mutastein producing ability regardless of whether or not it is a variety or a variant of the above mentioned strain.

Mutastein can be produced in a culture medium by culturing the Mutastein-producing strain aerobically in accordance with a generally known method for a fungus. For instance, the Mutastein-producing strain can be subcultured on a potato dextrose agar medium, and then for the production of Mutastein, the mycelium grown on this agar medium can directly be inoculated to a production medium and cultured therein. Alternatively, the strain grown in a production medium can be transplanted to a fresh production medium and also cultured therein for the production of Mutastein.

The Mutastein-producing strain can grow at a temperature within a range of from 7 to 35° C. However, for the production of Mutastein, a temperature of from 20° to 30° C. is usually preferred. For the culture of the Mutastein-producing Aspergillus strains, it is possible to use the nutrient sources which are commonly known for the culture of fungi or other microorganisms. For instance, glucose, maltose, textrin, starch, lactose, saccharose, glycerine, and the like can be used as a carbon source. Among these carbon sources, glucose and glycerine are the particularly preferable carbon sources for the production of Mutastein.

All of the nitrogen sources known to be useful for the growth of fungi and other microorganisms, can be used for the production of Mutastein. For instance, peptone, meat extract, yeast, yeast extract, soy bean powder, peanut powder, corn steep liquor, rice bran, and inorganic nitrogen sources, can be used.

An inorganic salt or a metal salt may be added, if required, in the process of the Mutastein production by culturing the Mutastein-producing strains. Further, if required, a very small amount of a heavy metal may also be added.

Mutastein can generally be obtained by aerobical culture of the Mutastein-producing strain. For this purpose, an aerobic culture method may be commonly applied, which includes a solid culture method, a shaking culture method or an aeration-agitation culture method. If defoaming is required during the culturing or the sterilization of the culture medium, a defoamer such as silicone oil or other surface active agents may be used. The culturing temperature is preferable from 20° to 30° C.

The physiological activities of Mutastein is determined by the plaque formation method which is mentioned below. Namely, 10 ml of a culture medium is put in a test tube, and a nichrome wire (20 gage) is placed therein to inoculate Streptococcus mutans which is a cariogenic baceterium (i.e. a tooth decaying strain). After the incubation at 37° C. for a predetermined period of time (for instance, after 48 hours), the amount of the plaque deposited on the nichrome wire is measured. By comparing the plague amount in the case where a predetermined amount of Mutastein is added, with a control containing no Mutastein, the physiological activities of Mutastein can be determined (R. M. McCabe, P. H. Keyes, A. Howell, Jr., Arch. Oral. Biol., Vol. 12, pages 1653 to 1656, 1967).

The culturing is continued until Mutastein is substantially accumulated, and as explained in the Examples hereinafter, the isolation by extraction of the substance from the culture medium can be conducted by proper combinations of various methods based on the characteristics of the substance which have been made clearly known by the present inventor. Namely, there may be used a salting out method with use of e.g. ammonium sulfate, a pH precipitation fractionation method based on the control of the pH, various ion exchange chromatography methods, a gel-filtration method with use of various carriers, various electrophoreses, an ultrafiltration method, a freezedrying method, a dialysis, and an extraction treatment with use of various organic solvents. Mutastein can be isolated by using these methods in a proper combination or by repeating one of these methods.

Figure 2:
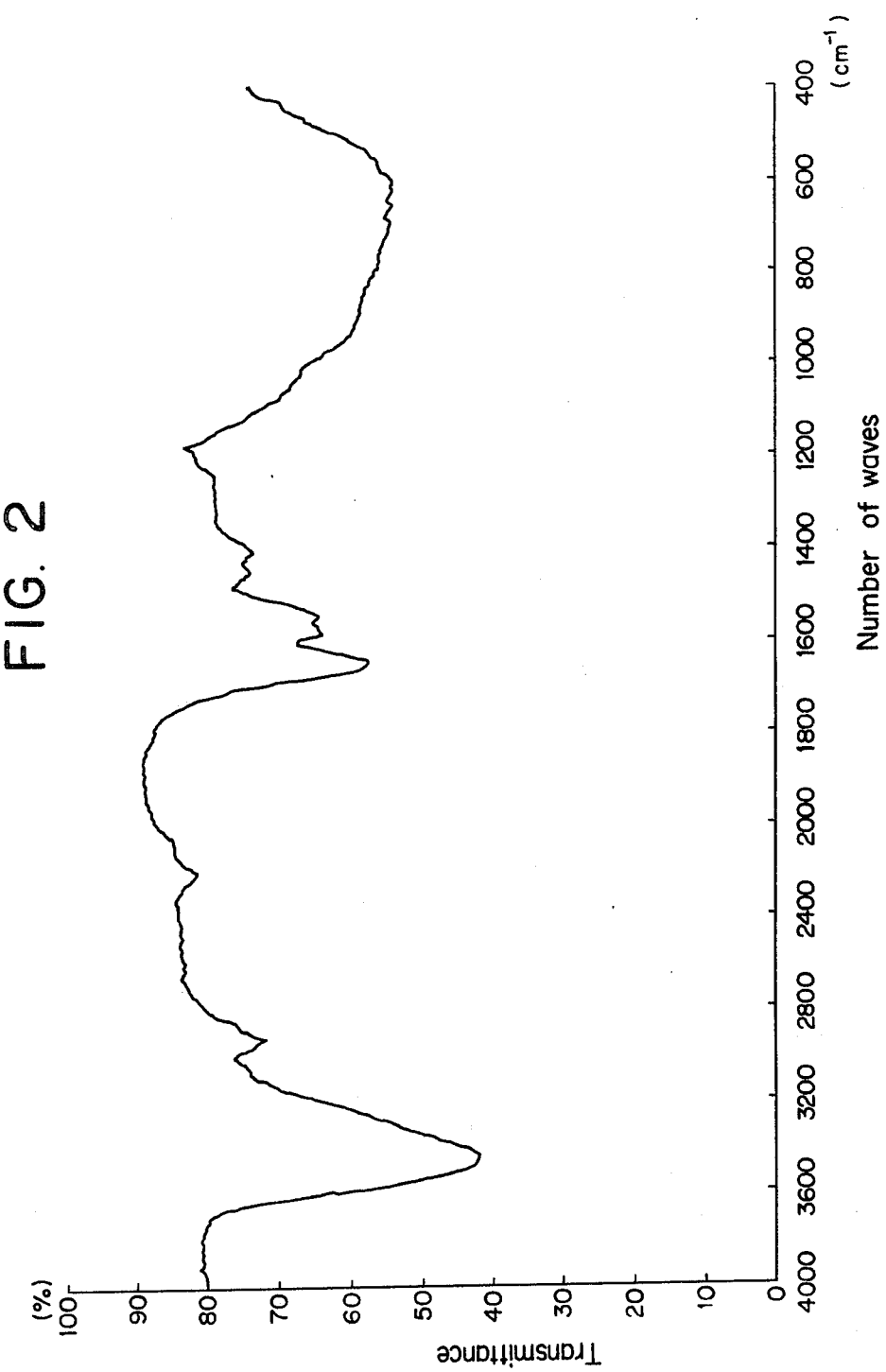
FIG. 2 shows the infrared absorption spectrum of the same substance.

Now, the physicochemical properties and the biological characteristics of Mutastein are as follows:

(1) it has a molecular weight of at least 200,000, and when subjected to gel-filtration with Sephadex G-100 and Sephallose 6B, it will be eluted in a void volume (2) its ultraviolet spectrum: FIG. 1, (3) its infrared spectrum: FIG. 2, (4) it has a proteinous nature and contains about 10% of saccharide, (5) it is soluble in water and a salt solution, but it can be salted out from an ammonium sulfate solution at 30% saturation; and it is insoluble in acetone, ethanol, ethyl acetate and benzene, (6) it is soluble in a buffer solution above pH 7, but it precipitates at a pH of from 3 to 3.5, (7) it is stable when heat-treated at pH 9, at 100° C. for 10 minutes, (8) its elementary analysis:
C: about 44%, H: about 7%, and N: about 12%, (9) its colour reactions:
Phenol-sulfuric acid colour reaction (orange), anf Folin's colour reaction (blue),

(10) In the physiological activity test in which, as mentioned precedingly, the plaque formation of Streptococcus mutans 6715 was observed, it inhibits the plaque formation in a concentration of above 10 µg/ml,

(11) The acute toxicity ($LD_{50}$) by its oral administration to a mouse is above 1 g/kg.

Various studies have been made on the effects of Mutastein against the tooth tartar formation with use of animals, and as a result, its effectiveness has been confirmed. For instance, a group of five golden hamsters were infected with Streptococcus mutans 6715 and fed with a high saccharose feed (diet 2000) (H. V. Jordan, P. H. Keyes, Archs. Oral Biol., Vol. 9, pages 377 to 384, 1964). On the other hand, another group of the hamsters were fed with the feed containing 1% of Mutastein. After 3 weeks of feeding, these two groups were compared with respect to the amount of the tooth tartar formation and the degree of decaying of the teeth. It was thereby found that in the Mutastein administered group, the amount of the tooth tartar formation was significantly less than that in the group to which no Mutastein was administered, and the degree of the decaying of the teeth was also reduced.

Thus, Mutastein has inhibiting effects against the tooth tartar formation and against the tooth decay. It can be used, for instance, for medical, Drug Quasi, or food additives, or as a preventive agent against the tooth decay.

Mutastein may be orally administered, for instance, in the form of capsules, tablets, etc. Normally, the oral administration is suitable. The dosage varies depending upon the age, symptom and weight, but usually, for an adult, it may be administered in an amount of about 1 to 1000 mg per day in 1 to 3 times a day. However, it may be administered in a greater amount or in a greater number of times, as the case requires.

Now, Examples of the present invention will be given, below. However, it should be understood that various modifications are possible in collecting Mutastein from the culture or its related based on the knowledge of the above mentioned characteristics which have been made clearly known by the present invention. The present invention should not be limited to these Examples, and includes all the methods which are readily derivable from the findings described in this specification.

EXAMPLE 1

*Aspergillus terreus* M 3328 was inoculated to a culture medium containing 1% of glucose, 2% of starch, 2% of soy bean meal, 0.1% of potassium mono-phosphate, and 0.05% of magnesium sulfate ($MgSO_4.7H_2O$) and cultured aerobically at a temperature of 25° C. for 9 days. The filtered culture solution thereby obtained (3.6 l) was saturated with 30% of ammonium sulfate, and the precipitates thereby formed were collected by centrifugal separation and sufficiently dialyzed against 5 mM phosphate buffer (pH 7.1). Then, the dialyzed inner solution was brought to pH 3.5 with diluted hydrochloric acid, and the precipitates thereby formed were collected by centrifugal separation and sufficiently dialyzed against 5 mM phosphoric acid buffer (pH 6.9) containing 0.1 M sodium chloride. The dialyzed inner solution was applied to a column of Sephallose 6B prepared with the same buffer containing 0.1 M sodium chloride, and developed to isolate the active fraction. This active fraction was sufficiently dialyzed against distilled water, and then freeze-dried, whereupon slightly white purified Mutastein (1.8 g as a protein) was obtained.

What is claimed is:

1. A physiologically active substance identified as Mutastein having the following physiochemical properties:
   (1) a molecular weight of at least 200,000, and said Mutastein, when being subjected to gel-filtration over Sephadex G-100 or Sephallose 6B, is eluted in the void volume;
   (2) the ultraviolet spectrum of FIG. 1;
   (3) the infrared spectrum of FIG. 2;
   (4) said Mutastein having a proteinaceous nature and containing about 10% of a saccharide;
   (5) said Mutastein being soluble in water and a saline solution, but being salted out from a saturated solution containing about 30% of ammonium sulfate; said Mutastein being insoluble in acetone, ethanol, ethylacetate and benzene;
   (6) said Mutastein being dissolvable in a buffer solution having a pH of at least 7, but precipitating from solution at a pH of from 3 to 3.5;
   (7) said Mutastein being stable when heat-treated at pH 9 at 100° C. for 10 minutes;
   (8) an elemental analysis of: C: about 44%, H: about 7% and N: about 12%,
   (9) color reactions yielding an orange color to the Phenol-sulfuric acid color reaction and blue to the Folin's color reaction.

2. A process for producing the physiologically active substance Mutastein as defined in claim 1 which comprises:
   culturing the Mutastein-producing strain belonging to the genus Aspergillus, having the identifying characteristics of FERM BP-101, in a medium until a sufficient amount of Mutastein is produced; and collecting the Mutastein from the culture medium.

3. The process as claimed in claim 2, wherein the culture is effected aerobically at temperatures of from 20° to 30° C.

4. The process as claimed in claim 3, wherein the temperature is in the range of from 24° to 28° C.

5. The process as claimed in claim 2, wherein the culture is effected at pH 2 to 8.

6. The process as claimed in claim 5, wherein the pH is in the range of from 3 to 7.

7. The process as claimed in claim 2, wherein the culture is effected by first subculturing said strain on a potato-dextrose-agar medium, and inoculating the mycelium grown on this agar medium to a production medium and culturing it therein.

8. A tooth decay preventing composition comprising: a bacterial dextran synthesis inhibiting amount of the substance Mutastein of claim 1 and a pharmaceutically acceptable carrier, for oral administration, in the form of a capsule or a tablet.

* * * * *